United States Patent [19]

Hallgren

[11] Patent Number: 4,471,133

[45] Date of Patent: Sep. 11, 1984

[54] CONTINUOUS METHOD FOR MAKING METHYLDIMETHOXYSILANE

[75] Inventor: John E. Hallgren, Scotia, N.Y.

[73] Assignee: General Electric Company, Schenectady, N.Y.

[21] Appl. No.: 499,589

[22] Filed: May 31, 1983

[51] Int. Cl.$^3$ ............................. C07F 7/08; C07F 7/18
[52] U.S. Cl. .................................................. 556/471
[58] Field of Search ....................................... 556/471

[56] References Cited

U.S. PATENT DOCUMENTS

| 3,567,756 | 3/1971 | Rothe | 556/471 |
| 3,985,781 | 10/1976 | Kötzsch et al. | 556/471 X |
| 4,060,538 | 11/1977 | Kötzsch et al. | 556/471 X |
| 4,228,092 | 10/1980 | Kotzsch et al. | 556/471 |
| 4,234,502 | 11/1980 | Kappler et al. | 556/413 |

OTHER PUBLICATIONS

R. Fessenden et al., Chem. Rev., The Chemistry of Silicon-Nitrogen Compounds, vol. 61, (1961), pp. 361–388.
Fink, Helv. Chem. Acta., Beitrage Zur Chemie der Si-N-Bindung, IX[1][2] Silane als Silylierungsmittel in der Silicium–Stickstoff-Chemie, vol. 59, (1966), pp. 1408–1415.
Klebe, Adv. Org. Chem., Silylation in Organic Synthesis, vol. 8, (1972), pp. 97–178.

Primary Examiner—Paul F. Shaver
Attorney, Agent, or Firm—William A. Teoli; James C. Davis, Jr.; James Magee, Jr.

[57] ABSTRACT

A method is provided for making polymethoxyhydrosilane in a continuous manner by effecting contact between a polychlorohydrosilane and liquid methanol in a vertical reactor resulting in the production of hydrogen chloride which is allowed to separate on formation and a bottoms reaction product consisting essentially of polymethoxyhydrosilane which is thereafter distilled to effect the separation and recovery of the polymethoxyhydrosilane. Polymethoxyhydrosilane is used as an intermediate for the production of hybrid methoxysilanes, such as polymethoxyaminosilanes and polymethoxysilylenolethers useful as end-capping silanes for making noncorrosive RTV compositions.

3 Claims, 1 Drawing Figure

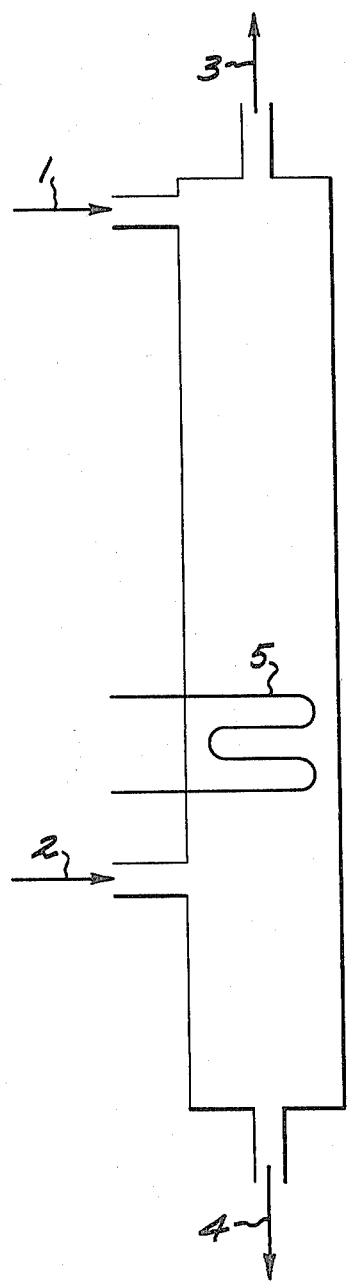

CONTINUOUS METHOD FOR MAKING METHYLDIMETHOXYSILANE

CROSS REFERENCE TO RELATED APPLICATIONS

Reference is made to my copending application Ser. No. 499,639, filed May 31, 1983, filed concurrently herewith, assigned to the same assignee as the present invention and incorporated herein by reference.

BACKGROUND OF THE INVENTION

Prior to the present invention, polymethoxyhydrosilanes having the formula,

where R is selected from $C_{(1-13)}$ monovalent hydrocarbon radicals and substituted $C_{(1-13)}$ monovalent hydrocarbon radicals and a has a value of 0 or 1, were prepared in a batch process by reacting polychlorohydrosilane of the formula,

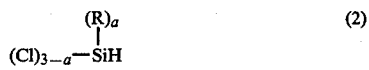

with methanol, as shown by F. Taurke, Ber. 38 1661 (1905), M. E. Havill, I. Joffe and H. W. Post, *J. Org. Chem.* 13 289 (1948), Ger. Offen. No. 2,409,731 and H. J. Kotzch et al U.S. Pat. No. 4,228,092. Although high yields of polymethoxyhydrosilanes of formula (1) can be obtained by such batch procedures, experience has shown that such methods cannot be extended to a continuous process due to various side reactions which often results in the loss of hydrogen bonded to silicon.

The present invention is based on my discovery that if methanol is allowed to contact polychlorohydrosilane vapor and the resulting hydrogen chloride is immediately separated from the polymethoxysilane reaction product, polymethoxyhydrosilane can be made at high yields. A preferred procedure is to effect contact between methanol and polychlorohydrosilane vapor in a vertical reactor such as shown by the drawing, allowing for the separation of a polymethoxysilane bottoms product, and the recovery of the desired polymethoxyhydrosilane as a distillation product.

STATEMENT OF THE INVENTION

There is provided by the present invention a method for making polymethoxyhydrosilane of formula (1) in a continuous manner which comprises (A) effecting contact between methanol and vaporous polychlorohydrosilane of formula (2) in a continuous manner to allow for the formation of polymethoxyhydrosilane and the continuous separation of hydrogen chloride as it is formed, (B) continuously recovering the polymethoxyhydrosilane reaction production produced in (A), and (C) continuously distilling the recovered polymethoxyhydrosilane reaction product of (B) to effect the separation and recovery of the polymethoxyhydrosilane.

Radicals included by R of formulas (1) and (2) are, for example, $C_{(1-8)}$ alkyl radicals such as methyl, ethyl, or vinyl.

Polychlorosilanes included within formula (2) are, for example, methyldichlorosilane, ethyldichlorosilane, dimethylchlorosilane, vinyldichlorosilane, etc.

Polymethoxyhydrosilanes included within formula (1), are, for example, methyldimethoxysilane, ethyldimethoxysilane, vinyldimethoxysilane, dimethylmethoxysilane, etc.

Reference to the FIGURE showing a vertical reactor such as a packed column, where methanol can be introduced in a continuous manner at 1 and polychlorosilane vapor can be fed into the column at 2 and hydrogen chloride is removed at 3 and a polymethoxysilane reaction product is removed at 4. A heating coil is shown at 5.

In the practice of the invention, methanol can be continuously introduced at the top of a vertical packed reactor and allowed to trickle down to the reactor where contact can be made with polychlorosilane vapor at temperatures in the range of from 50° C. to 120° C. and preferrably from 55° C. to 65° C. Hydrogen chloride can be continuously separated at the top of the reactor, while polymethoxysilane can be continuously separated at the bottom of the reactor. Distillation in a continuous manner of the aforementioned bottoms product can be effected at temperatures of from 60° C. to 100° C. and pressures from 1 to 5 atmospheres.

In order that those skilled in the art will be better able to practice the invention, the following example is given by way of illustration and not by way of limitation. All parts are by weight.

EXAMPLE

Methanol is pumped at a rate of 1 ml per minute into the top of a packed 60 centimeter times 1 centimeter vertical glass column fitted with a dry ice reflux condenser. The column was packed with 8 millimeter glass beads which were maintained at 60° C.±1° C. via an external jacket through which water was circulated. Methyldichlorosilane vapor was introduced 40 centimeters from the top of the column at a rate of 0.60 grams per minute. Hydrogen chloride which formed upon contact between methanol and methyldichlorosilane was separated at the top of the column while a bottoms product was collected in a flask attached to the bottom of the column.

The bottoms mixture was distilled and the first cut having a boiling range of from 40°-60° C. consisted mostly of methylmethoxychlorosilane with some methyldichlorosilane. This first distillation cut was recycled as feed. The second cut boiling at 60°-61° C. consisted of pure methyldimethoxysilane. The pot residue was found to be nearly pure trimethoxymethylsilane. There was obtained a 77% conversion of chlorinated silane to methoxy silane. The following shows the product analysis of the bottoms product:

| Product | Mol % |
| --- | --- |
| MeSiH(OMe)$_2$ | 62 |
| MeSiH(OMe)Cl | 30 |
| MeSiHCl$_2$ | 5 |
| MeSi(OMe)$_3$ | 2 |
| MeSiH(OMe)$_2$Cl | trace |

The above results based on GC analysis shows 98% yield of methoxysilane without a significant loss of hydrogen attached to silicon.

Although the above results are directed to only a few of the very many variables which can be used in the practice of the present invention, it should be understood that the present invention is directed to a much broader variety of reactants and conditions as shown in the description preceding this example.

What I claim as new and desire to secure by Letters Patent of the United States is:

1. A method for making polymethoxyhydrosilane of the formula,

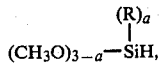

in a continuous manner which comprises, (A) effecting contact at a temperature of from 50° C. to 120° C. between methanol and vaporous polychlorohydrosilane of the formula,

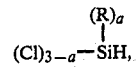

in a continuous manner to allow for the continuous separation of hydrogen chloride as it is formed, (B) continuously recovering the polymethoxyhydrosilane reaction production produced in (A), and (C) continuously distilling the recovered polymethoxyhydrosilane reaction product of (B) to effect the separation and recovery of the polymethoxyhydrosilane, where R is a member selected from the class consisting of methyl, ethyl and vinyl, and a has a value of 0 or 1.

2. A method in accordance with claim 1, where the polychlorohydrosilane is methyldichlorosilane.

3. A method in accordance with claim 1, which is practiced in a vertical packed reactor.

* * * * *